United States Patent [19]

Wurtman

[11] 4,377,595

[45] Mar. 22, 1983

[54] PROCESS FOR REDUCING DEPRESSION

[75] Inventor: Richard J. Wurtman, Waban, Mass.

[73] Assignee: Massachusetts Institute of Technology, Cambridge, Mass.

[21] Appl. No.: 154,189

[22] Filed: May 29, 1980

Related U.S. Application Data

[63] Continuation of Ser. No. 66,158, Aug. 13, 1979, which is a continuation-in-part of Ser. No. 898,740, Apr. 24, 1978, abandoned.

[51] Int. Cl.$^3$ .......................................... A61K 31/195
[52] U.S. Cl. .................................................. 424/319
[58] Field of Search ........................................ 424/319

[56] References Cited

U.S. PATENT DOCUMENTS 3,651,237  3/1972  Laborit ............................... 424/319

*Primary Examiner*—Stanley J. Friedman
*Attorney, Agent, or Firm*—Arthur A. Smith, Jr.; Paul J. Cook

[57] ABSTRACT

The level of norepinephrine in neuronal synapses is regulated in order to treat depression by administering a neutral amino acid composition to a human wherein an increased brain level of norepinephrine is effected when the composition contains increased amounts of tyrosine and/or phenylalanine. Increased or decreased brain levels of serotonin are obtained when the amino acid composition contains increased or decreased amounts of tryptophan.

The neutral amino acid composition can be administered alone or concomitantly with a drug which increases or decreases noradrenergic neurotransmission.

2 Claims, 1 Drawing Figure

PROCESS FOR REDUCING DEPRESSION

The Government has rights in this invention pursuant to Grant No. AM-14228 awarded by the National Institute of Health.

REFERENCE TO RELATED APPLICATIONS

This is a continuation of application Ser. No. 066,158 filed Aug. 13, 1979, which is a continuation-in-part of Ser. No. 898,740 filed Apr. 24, 1978, now abandoned.

BACKGROUND OF THE INVENTION

This invention relates to a method and composition for treating depression in humans by increasing the level of norepinephrine in neuronal synapses.

It is well known that the neutrotransmitters dopamine and nonrepinephrine are derived from dihydroxyphenylalanine (DOPA). DOPA is, in turn, produced in neurons by the enzymatic hydroxylation of the amino acid tyrosine. This process is catalyzed by the enzyme tyrosine hydroxylase. The DOPA is decarboxylated to dopamine by the enzyme aromatic L-amino acid decarboxylase (AAAD) and norepinephrine is produced from dopamine in neurons that also contain the enzyme dopamine betahydroxylase. It is also known that within this reaction chain, the rate-limiting step is the conversion of tyrosine to DOPA. For this reason, DOPA has been administered to patients who suffer medical disability resulting from dopamine deficiency in diseases such as Parkinson's Disease. Unfortunately, DOPA, when administered, is taken up by cells throughout the body and converted to dopamine and this interferes with the normal metabolic processes in these other cells. In addition, DOPA interferes with the body's normal storage of the neurotransmitter serotonin, and lowers brain levels of the compound S-adenosylmethionine. It is believed that these effects contribute to such unwanted side-effects as the "On-Off Phenomenon" and, in some patients, psychotic symptoms. Other types of drugs that act by increasing dopamine and norepinephrine levels in synapses include the Monoamine Oxidase Inhibitors (which slow the destruction of these neurotransmitters) and the tricyclic antidepressants; these compounds, which are used in treating diseases like depression, also relatively non-specific—producing many chemical effects besides increasing synaptic dopamine and norepinephrine levels and thus have a range of unwanted side-effects such as the dangerous increases in blood pressure that occur when people receiving monoamine oxidase inhibitors eat certain foods.

Other diseases appear to be caused by the presence of excessive quantities of dopamine or norepinephrine within synapses including psychosis (too much dopamine), and hypertension and cardiac arrhythmias (too much norepinephrine released from sympathetic neurons). These diseases now usually are treated by drugs that block the interactions of dopamine or norepinephrine with their post-synaptic receptors, such as phenothiazines or butyrophenones. However, these agents all exhibit some non-specific actions as well, and thus cause side-effects.

Prior attempts to increase or decrease the levels of dopamine or norepinephrine by modifying neuronal tyrosine levels had been deemed unsuccessful because the total amounts of these compounds in brains and tissues were not noted to change. It was first observed in Wurtman et al. (Science 185:183-184, July 12, 1974) that increases in brain DOPA concentrations, which, under the conditions of the experiments, varied in proportion to the rates at which dopamine and norepinephrine were being synthesized could be obtained by increasing brain tyrosine concentrations, and that decreases in brain DOPA concentrations could be produced by giving rats treatments that decreased brain tyrosine. An example of a treatment that increased brain tyrosine was the administration of tyrosine itself; an example of a treatment that decreased brain tyrosine was the administration of one of the other neutral amino acids, e.g., leucine, that competes with plasma tyrosine for uptake into the brain. Prior to that disclosure, it had been believed that the rate-limiting enzyme, tyrosine hydroxylase, was so saturated with tyrosine, that increases or decreased in brain tyrosine levels would not affect tyrosine's conversion to DOPA. In neither the above Wurtman et al. article nor a subsequent paper by Gibson and Wurtman (Biochem. Pharmacology, 26:1137–1142, June, 1977) was it actually shown that such changes in DOPA accumulation were accompanied by changes in brain dopamine or norepinephrine levels. Furthermore, in neither was it shown that changing brain tyrosine levels had any effect on the amounts of dopamine or norepinephrine released into synapses.

It would be highly desirable to provide a means for increasing the amounts of norepinephrine that actually are present within synapses. Such changes in synaptic transmitter levels need not be associated with changes in the total amount of norepinephrine present in the brain or other tissues, inasmuch as it is now well known that not all of the molecules of the transmitters that are stored in neurons are equally accessable for release into synapses. Furthermore, it would be desirable to provide such a means which is biochemically specific and which lacks the undesirable side effects associated with administration of DOPA, and MAO inhibitors, the phenothiazines, and the other drugs described above. Such a means might by itself be therapeutic in the treatment of depression. Alternatively, it could be used in combination with drugs now used to treat depression to amplify their therapeutic effects.

SUMMARY OF THE INVENTION

The present invention provides a method for treating depression associated with a deficiency of norepinephrine in synapses. This invention is based upon the discovery that treatments that increase neuronal tyrosine levels can also cause corresponding increases in the amounts of norepinephrine released into synapses. The tyrosine, and its precursor, phenylalanine, can be administered alone or in admixture, with other neutral amino acids with or without drugs, in order to raise or lower brain tyrosine (and phenylalanine) levels, and thereby to treat depression associated with deficiency of norepinephrine in synapses. By varying the proportion of tryptophan, another amino acid, in the mixture, the synthesis and synaptic release of serotonin, another brain neurotransmitter, can similarly be controlled. Increased synaptic norepinephrine levels are obtained by giving tyrosine regardless of whether the norepinephrine-releasing neurons are or are not especially active. Decreases in norepinephrine release into synapses can be obtained by lowering brain tyrosine levels by administering neutral amino acid compositions low in tyrosine levels. Decreases in serotonin release can similarly be obtained by lowering brain tryptophan levels. By regulating the proportion of tyrosine in a given mixture of neutral amino acids, it can be caused to increase or decrease norepinephrine release. Phenylalanine can, in low doses, be used in place of tyrosine. Tryptophan's proportion in the neutral amino acid mixture can be used to regulate serotonin's release into synapses while regulating norepinephrine release as described herein.

DETAILED DESCRIPTION OF SPECIFIC EMBODIMENTS

Figure 1:
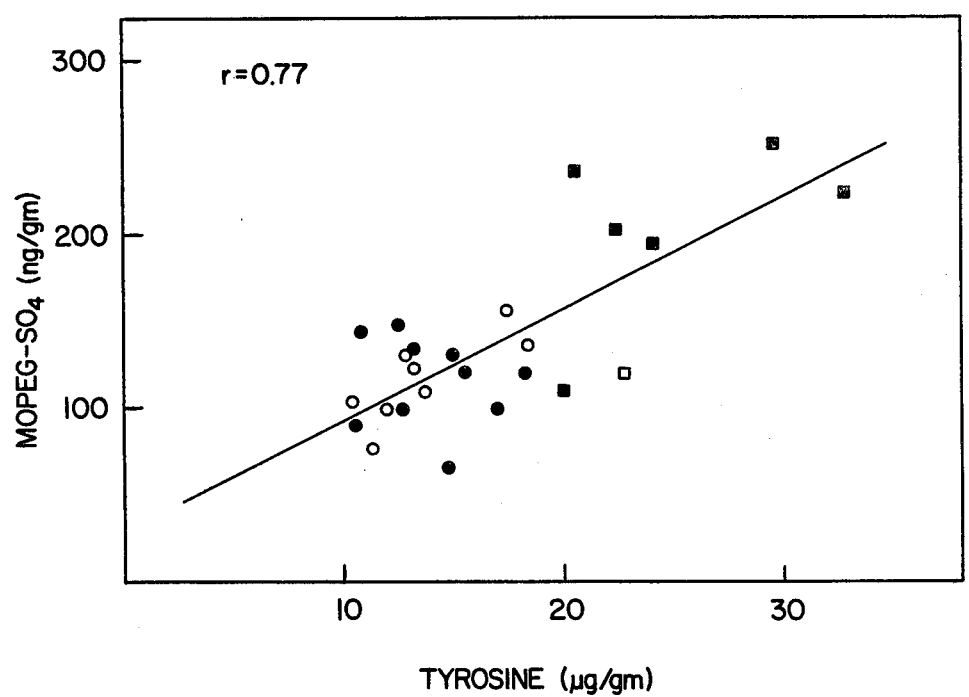

In accordance with this invention, tyrosine and/or phenylalanine and/or other neutral amino acids is administered to a patient either alone or in combination with one or more drugs thereby to increase the level of norepinephrine which is released into synapses. Serotonin release also can be controlled at the same time by varying the proportion of tryptophan present in the amino acid mixture. Release of norepinephrine or serotonin into synapses can be varied using amino acid mixtures whether or not the norepinephrine-releasing or serotonin-releasing neurons are especially active. Similarly, decrease in norepinephrine release can be produced by administering amino acid mixtures that compete with tyrosine for uptake for the brain thereby decreasing brain tyrosine levels.

The composition of the amino acid mixture that is utilized depends upon the nature of the illness in the patient that is to be treated. When there is need to increase norepinephrine release without increasing that of serotonin, tyrosine (and/or phenylalanine) is administered, with or without other amino acids not including serotonin's precursor, tryptophan, in doses ranging between 5 mg/kg and 200 mg/kg. This therapy is useful, alone or as an adjunct to drug therapies, in treating certain types of depression. In some situations, phenylalanine can be used as a substitute for tyrosine, inasmuch as much of this amino acid is converted to tyrosine in the liver, and released into the blood stream for uptake into the brain. However, plasma phenylalanine levels should be less than about double those of tyrosine, since at the higher levels, phenylalanine competes with tyrosine for uptake into the brain, and can inhibit the enzyme tyrosine hydroxylase.

In some instances, it may be desirable to treat depression by also increasing brain serotonin levels while increasing norepinephrine release since it appears that increasing brain serotonin levels tend to reduce depression. In these instances, the compositions administered also contain tryptophan in addition to tyrosine and/or phenylalanine and other neutral amino acids. Other neutral amino acids than these compositions can contain include the branched-chain amino acids (leucine, isoleucine, valine), as well as methionine, threonine, and histidine. The amino acids can be supplied as monomers or as natural or synthetic polymers, e.g., peptides. The phenylalanine, tryptophan and tyrosine will be referred to collectively as "the useful amino acids".

The ratios of the plasma concentrations of tyrosine, phenylalanine and tryptophan to the sum of the other neutral amino acids are normally about 0.08–0.12, 0.07–0.12 and 0.06–0.14 respectively, depending on the composition of the diet. In some diseases, e.g., cirrhosis of the liver leading to coma; diabetes; hyperinsulinism; such catabolic states as starvation, cachexia, disseminated cancer, or severe burns or trauma, these ratios are abnormal, causing changes in brain dopamine, norepinephrine and serotonin release. The particular compositions used in these situations are designed to restore the plasma ratios to normal. In the primarily neurologic or psychiatric diseases listed above, the goal of amino acid therapy is to raise or lower these ratios above or below their normal ranges, in order to increase or decrease the release of norepinephrine (or serotonin) into synapses.

The tyrosine, phenylalanine and other neutral amino acids can be administered as free amino acids, esters, salts, natural or synthetic polymers, or as constituents of foods. The route of administration can be oral or parenteral, e.g., intravenous.

The following examples illustrate the present invention and are not intended to limit the same.

EXAMPLE I

This example illustrates that brain norepinephrine can be synthesized by increasing brain tyrosine levels.

This example shows that the rate at which 3-methoxy-4-hydroxy-phenylethyleneglycol-sulfate (MOPEG-$SO_4$), the major brain metabolite of norepinephrine, accumulates in rat brain also varies as a function of brain tyrosine levels. This shows that brain tyrosine levels affect not only the synthesis, but also the turnover and release of brain norepinephrine.

Male Sprague-Dawley rats (Charles River Breeding Laboratories, Wilmington, Mass.) weighing 150 g were housed in hanging cages (6–8 per cage), given ad libitum access to tap water and a 26% protein diet (Charles River Rat-Mouse-Hamster Maintenance Formula 24RF), and maintained under light (300 microwatts/$cm^2$; Vita-Lite, Duro-Test Corp., North Bergen, N.J.) between 8 AM and 8 PM daily. Rats used for diet experiments were fasted overnight and then allowed to consume the experimental diet starting at 10 AM. Diets of different compositions were prepared in agar gel (35 g/100 ml of water) as described by Gibson et al., Biochem. Pharmacol., 26, 1137–1142 (1977). All amino acids and drugs were injected intraperitoneally.

Norepinephrine synthesis and turnover in brain neurons were estimated by measuring the rate of accumulation of MOPEG-$SO_4$ after probenecid administration or exposure to a cold environment. The MOPEG-$SO_4$ in brain homogenates was isolated using an anion exchange column (A-25 DEAE Sephadex; Pharmacia, Piscataway, N.J.); the method used was basically that of Meek and Neff, Br. J. Pharmacol., 45, 435–441 (1972), but modified to allow both tyrosine and MOPEG-$SO_4$ to be measured in the same sample. An aliquot of each homogenate (in 0.15 M $ZnSO_4$) was first assayed for tyrosine by the method of Waalkes and Udenfriend, J. Lab. Clin. Med., 50, 733–736 (1957). An equal volume of 0.15 M barium hydroxide was then added to the remaining homogenate, which was rehomogenized (Polytron, Brinkman Instruments, N.Y.), centrifuged and assayed for MOPEG-$SO_4$ by the method of Meek and Neff above. Recoveries of MOPEG-$SO_4$ and tyrosine from whole brain homogenates were 70–75% and 85–95%, respectively.

Tyrosine (Grand Island Biological Co., Long Island, N.Y.) and probenecid (Sigma Chemical Co., St. Louis, MO), which are poorly soluble in water, were dissolved in dulte NaOH; the solutions were then buffered to pH 7.4 with hydrochloric acid and brought to a known volume with saline. This yielded a fine suspension that was suitable for injection.

In experiments on stress produced by exposure to cold, animals received the more soluble ethyl-ester form of tyrosine (J. T. Baker, Phillipsburg, N.J.), instead of tyrosine itself, to raise brain tyrosine levels. Data were analyzed by one-way or two-way analysis of variance.

Probenecid treatment significantly raised the MOPEG-SO$_4$ level in brain from 123 ng/g in diluent-injected controls to 175 ng/g in probenecid-treated animals ($P<0.001$) (Table I). Tyrosine administration alone had no effect on brain MOPEG-SO$_4$; however, pretreatment with this amino acid significantly enhanced the probenecid-induced rise in MOPEG-SO$_4$ (to 203 ng/g, as compared with 175 ng/kg in rats receiving probenecid alone ($P<0.01$; Table I).

TABLE I

Accumulation of MOPEG—SO$_4$ after Probenecid Administration and Pretreatment with tyrosine

| Pretreatment | Brain Tyrosine Level ($\mu$g/g) | | Brain MOPEG—SO$_4$ Level (ng/g) | |
|---|---|---|---|---|
| | Diluent | Probenecid | Diluent | Probenecid |
| Diluent | 13.9 ± 0.5 | 15.7 ± 0.7 | 123 ± 6 | 175 ± 6 |
| Tyrosine | 23.3 ± 1.5 | 24.7 ± 1.3 | 127 ± 2 | 203 ± 8 |

Note: In each of 3 experiments, groups of 4–6 rats were injected with either a dose of tyrosine (100 mg/kg, i.p.) known to accelerate brain dopa synthesis or its diluent and, 30 min. later, with probenecid (400 mg/kg, i.p.) or its diluent. Animals were killeed 60 min. after the second injection, and their whole brains were analyzed for tyrosine and MOPEG-SO$_4$. Tyrosine administration significantly raised brain tyrosine levels ($P\pm0.001$, whereas probenecid failed to modify brain tyrosine or its response to exogenous tyrosine. Probenecid significantly raised brain MOPEG-SO$_4$ ($P\pm0.001$), and tyrosine pretreatment significantly enhanced this response ($P\pm0.01$). Data were analyzed by two-way analysis of variance. Values are expressed as means±SEM.

Placing the rats in a cold environment (4° C.) increases norepinephrine turnover; this accelerates the formation of both norepinephrine itself and its metabolite, MOPEG-SO$_4$, in brain neurons. The rates were exposed to cold to deetermine whether treatments that changed brain tyrosine levels could influence the rate at which the brain accumulates MOPEG-SO$_4$ in rats exposed to cold stress and not given probenecid (FIG. 1).

Exposure to cold for 1 hour increased brain MOPEG-SO$_4$ levels by about 40% (from 80 ng/g to 114 ng/g; $P<0.01$). In animals treated with either of the amino acids or with saline, brain tyrosine levels paralleled, and were significantly correlated with, those of MOPEG-SO$_4$ ($r=0.77$, $P<005$; FIG. 1). Pretreatment with tyrosine raised brain tyrosine levels by about 80% (from 13.3 $\mu$g/g, in saline-injected animals, to 24.6 $\mu$g/g; $P<0.01$) and those MOPEG-SO$_4$ by 70% (from 114 ng/g to 193 ng/g; $P<0.01$). Pretreatment with valine failed, in this study, to cause significant alterations in brain tyrosine or MOPEG-SO$_4$ levels (14.3 $\mu$g/g and 117 ng/g, respectively); however, brain tyrosine and MOPEG-SO$_4$ levels were also significantly correlated in these animals, as in other experimental groups (FIG. 1).

The relationship shown in FIG. 1 was obtained as follows: Groups of rats were injected intraperitoneally with valine (200 mg/kg), an amino acid that competes with tyrosine for uptake into the brain (8), or with tyrosine (125 mg/kg of the ethyl ester) or saline; 30 min. later they were placed in single cages in a cold (4° C.) environment. After 1 hour, all animals were killed, and their whole brains were analyzed for tyrosine and MOPEG-SO$_4$. Control animals were injected with saline and left at room temperature (22° C.), also in single cages, for 90 min. Each point represents the tyrosine and MOPEG-SO$_4$ levels present in a single brain. Data were pooled from several experiments. Brain tyrosine and MOPEG-SO$_4$ levels in animals kept at room temperature were 14.6 $\mu$g/g and 80 ng/g, respectively. In FIG. 1, theee symbols are as follows: closed circles, animals pretreated with valine; open circles, animals pretreated with saline; closed squares, animals pretreated with tyrosine.

To determine whether physiologic variations in brain tyrosine level might also influence brain norepinephrine synthesis and turnover (as estimated by measuring MOPEG-SO$_4$ levels), the accumulation of this metabolite in animals exposed to a cold enviroment was examined after being allowed to consume a single meal that would be likely to elevate tyrosine levels.

Animals that had been fasted overnight were given access to either a protein-free (0% casein) or a 40% casein meal between 10 AM and 11 AM; they were then placed in the cold (4° C.) for 1 hour, after which they were killed, and their brains analyzed for tyrosine and MOPEG-SO$_4$. Fasted control animals remained at room temperature (22° C.) during this 2 hour period.

Exposure to cold accelerated the accumultion of MOPEG-SO$_4$ in brains of fasted rats, from 123 ng/g (in fasted control animals kept at 22° C.) to 163 ng/g ($P<0.05$); this treatment had no effect on brain tyrosine levels (10.1 $\mu$g/g vs. 10.5 g/g). Among animals placed in the cold, consumption of either a 0% or a 40% casein meal enhanced brain MOPEG-SO$_4$ accumulates by 40-50% (Table II; $P<0.01$). The 0% casein meal increased brain tyrosine by about 40% ($P<0.1$), whereas the 40% casein meal increased brain tyrosine by 77% ($P<0.01$).

When the consumption of a protein-free meal failed to evevate brain tyrosine levels, brain MOPEG-SO$_4$ levels also failed to rise (Table II). Among protein-fed animals in this study, the brain tyrosine level increased by about 50% (from 13.4 to 19.5 $\mu$g/g, $P<0.01$), and brain MOPEG-SO$_4$ rose in parallel.

These data's show that treatments that increased brain tyrosine levels can accelerate the accumultion of the norepinephrine metabolite MOPEG-SO$_4$ in the brains of rats pretreated with probenecid or exposed to a cold environment. Such treatments can be pharmacologic (i.e., intraperitoneal injection of tyrosine) or physiologic (i.e., consumption of a high-protein meal). They are compatible with the high Km of tyrosine hydroxylase for its substrate, relative to brain tyrosine concentrations. The enzyme is especially vulnerable to substrate limitation when it has been activated, inasmuch as activation selectively enhances its affinity for its cofactor.

MOPEG-SO$_4$ is the major metabolite of norepinephrine formed in ra brain and it is transported out of the brain by a probenecid-sensitive mechanism. After probenecid administration, MOPEG-SO$_4$ accumulates at a linear rate in rat brain for at least 60 min. Since brain norepinephrine levels remain constant during this interval, the rate of MOPEG-SO$_4$ accumulation provides a useful index of the rate of norepinephrine synthesis. This rate apparently is lower in unstressed, probenecid-treated rats than in animals placed in the cold (Tables I and II), however, in both circumstances, it is dependent on brain tyrosine levels.

TABLE II

Brain MOPEG—SO$_4$ Accumulation after Ingestion of a Single Protein-free or 40% Protein Diet among Rats Placed in a Cold Environment

| Treatment | Tyrosine (μg/g) | MOPEG—SO$_4$ (ng/g) |
|---|---|---|
| EXPERIMENT I | | |
| Fasted | 10.5 ± 0.55 | 163 ± 9 |
| Protein-free (0% Casein) | 14.4 ± 0.24* | 239 ± 17* |
| 40% Casein | 18.1 ± 0.85* | 228 ± 9* |
| EXPERIMENT II | | |
| Fasted | 13.4 ± 0.67 | 195 ± 9 |
| Protein-free (0)% Casein) | 13.3 ± 0.81 | 182 ± 18 |
| 40% Casein | 19.5 ± 1.03* | 264 ± 20* |

*Values are significantly different from corresponding fasted group (P < 0.01).
Values are significantly different from corresponding protein-free group (P < 0.01).

Note: Groups of 4-6 rats were fasted overnight and then allowed access to one of the test diets at 10 AM. At 11 AM, animals were placed in an environmental chamber at 4° C. for 1 hour. They were killed at noon, and their whole brains were analyzed for tyrosine and MOPEG-SO$_4$. Animals given protein-free and 40% protein diets consumed 9.7 and 10.5 g, respectively, in Experiment I, and 6.2 and 8.0 g in Experiment II. Data presented as means±SEM.

EXAMPLE II

This example illustrates that the administration of tyrosine to a patient suffering from depression significantly alleviates the depression.

A female middle-aged patient who has history of depression was alternately administered a placebo for three consecutive weeks followed by the administration of tyrosine for three consecutive weeks at a daily dosage of 3-6 grams per day. This schedule was repeated three times. The patient was tested for depression levels periodically during each three week period by Hamilton Depression Scores (the higher the score the greater the depression). The results are shown in Table III.

TABLE III

| Composition | Range of Hamilton Score |
|---|---|
| Placebo | 25 |
| Tyrosine (3-6 g/day) | 1-9 |
| Placebo | 24 |
| Tyrosine (3-6 g/day) | 13 |
| Placebo | 28 |
| Tyrosine (3-6 g/day) | 1-5 |

I claim:

1. The process for alleviating depression in a depressed human patient which comprises administering to the patient a neutral amino acid composition containing tyrosine in an amount effective to regulate blood plasma levels of tyrosine to form corresponding amounts of norepinephrine released in synapsis in the brain.

2. The process of claim 1 wherein the neutral amino acid composition contains tyrosine and tryptophan, the amount of tryptophan being sufficient to increase brain serotonin levels.